US008124030B2

(12) United States Patent
Sa

(10) Patent No.: US 8,124,030 B2
(45) Date of Patent: Feb. 28, 2012

(54) MICROFLUIDIC DEVICE HAVING REGULATED FLUID TRANSFER BETWEEN ELEMENTS LOCATED THEREIN

(75) Inventor: Brian Sa, Mountain View, CA (US)

(73) Assignee: The Regents of the University of California, Oakland, CA (US)

( * ) Notice: Subject to any disclaimer, the term of this patent is extended or adjusted under 35 U.S.C. 154(b) by 75 days.

(21) Appl. No.: 12/596,731

(22) PCT Filed: May 8, 2008

(86) PCT No.: PCT/US2008/063086

§ 371 (c)(1),
(2), (4) Date: Oct. 20, 2009

(87) PCT Pub. No.: WO2008/137997

PCT Pub. Date: Nov. 13, 2008

(65) Prior Publication Data

US 2010/0135859 A1 Jun. 3, 2010

Related U.S. Application Data

(60) Provisional application No. 60/916,774, filed on May 8, 2007.

(51) Int. Cl.

| | |
|---|---|
| ***B81B 1/00*** | (2006.01) |
| ***B01L 3/00*** | (2006.01) |
| ***C12M 1/10*** | (2006.01) |
| ***G05D 7/00*** | (2006.01) |

(52) U.S. Cl. ............ 422/506; 422/400; 422/501; 137/7; 435/286.5; 435/287.3; 436/45

(58) Field of Classification Search .......... 422/500–507, 422/400–403; 137/1, 7; 435/286.5, 287.3; 436/45

See application file for complete search history.

(56) References Cited

U.S. PATENT DOCUMENTS

| | | | | |
|---|---|---|---|---|
| 5,197,509 | A | 3/1993 | Cheng | |
| 6,619,311 | B2 * | 9/2003 | O'Connor et al. | 137/109 |
| 7,068,874 | B2 | 6/2006 | Wang et al. | |
| 7,309,467 | B2 | 12/2007 | Chen et al. | |
| 7,381,361 | B2 | 6/2008 | Sundararajan | |

(Continued)

OTHER PUBLICATIONS

PCT International Search Report for PCT/US2008/063086, Applicant: The Regents of the University of California, Form PCT/ISA/210 and 220, dated Aug. 20, 2008 (5 pages).

(Continued)

*Primary Examiner* — In Suk Bullock
*Assistant Examiner* — Timothy G Kingan
(74) *Attorney, Agent, or Firm* — Vista IP Law Group LLP

(57) ABSTRACT

A centrifugal microfluidic device includes a substrate configured for rotation about an axis, the substrate having a start chamber disposed therein, the start chamber configured to hold a liquid. The device includes an output chamber disposed in the substrate and located radially outward of the start chamber. A fluid transfer channel connects the start chamber to the output chamber. A ventilation channel connects the output chamber to the start chamber, the ventilation channel connecting at one end to a radially inward portion of the start chamber and at an opposing end to a junction point on the output chamber. A vent hole is provided in the substrate that is operatively connected to the output chamber. The location of the junction between the ventilation channel and the output chamber is located radially outward with respect to the level of fluid in the start chamber so as to prevent cross-contamination.

15 Claims, 6 Drawing Sheets

U.S. PATENT DOCUMENTS

| | | | | |
|---|---|---|---|---|
| 2004/0191125 | A1* | 9/2004 | Kellogg et al. | 422/72 |
| 2005/0084422 | A1* | 4/2005 | Kido et al. | 422/100 |
| 2007/0163647 | A1 | 7/2007 | Liu et al. | |

OTHER PUBLICATIONS

PCT Written Opinion of the International Search Authority for PCT/US2008/063086, Applicant: The Regents of the University of California, Form PCT/ISA/237, dated Aug. 20, 2008 (4 pages).

PCT International Preliminary Report on Patentability for PCT/US2008/063086, Applicant: The Regents of the University of California, Form PCT/IB/326 and 373, dated Nov. 19, 2009 (2 pages).

PCT Written Opinion of the International Searching Authority for PCT/US2008/06086, Applicant: The Regents of the University of California, Form PCT/ISA/237, dated Aug. 20, 2008 (4 pages).

* cited by examiner

MICROFLUIDIC DEVICE HAVING REGULATED FLUID TRANSFER BETWEEN ELEMENTS LOCATED THEREIN

REFERENCE TO RELATED APPLICATIONS

This Application is a U.S. National Stage filing under 35 U.S.C. X371 of International Application No. PCT/US2008/063086 filed on May 8, 2008, which claims priority of U.S. Provisional Patent Application No. 60/916,774 filed on May 8, 2007. The contents of the aforementioned applications are incorporated by reference as if set forth fully herein. Priority to the aforementioned application is hereby expressly claimed in accordance with 35 U.S.C. 119, 120, 365 and 371 and any other applicable statutes.

FIELD OF THE INVENTION

The field of the invention generally relates to microfluidic devices. More specifically, the field of the invention relates to microfluidic devices that are spun or rotated about an axis to effectuate fluid flow and/or transfer.

BACKGROUND OF THE INVENTION

Microfluidic devices are becoming increasingly more important in both research and commercial applications. Microfluidic devices, for example, are able to mix and react reagents in small quantities, thereby minimizing reagent costs. These same microfluidic devices also have a relatively small size or "footprint," thereby saving on laboratory space. For example, microfluidic devices are increasingly being used in clinical applications. Finally, because of their small scale, microfluidic devices are able to quickly and cost effectively synthesize products which can later be used in research and/or commercial applications.

In one type of microfluidic device, various microfluidic features such as channels, chambers, reservoirs, and the like are formed in a disk-shaped device. The disk may include, for instance, a Compact Disk (CD) having microfluidic features formed therein. This disk is then rotated about an axis or rotation (typically the center of the disk) to effectuate movement of fluid from one location to another. Rotation of the disk generally causes the flow of fluid to move toward the edges of the device. There is a need in these types of devices to regulate or modulate the flow of fluid from one location to another. In prior designs, there was no means to stop or otherwise affect fluid transfer once it had been initiated. This poses several problems including the possibility of cross-contamination when fluids from one reservoir or chamber backflow into other chambers or reservoirs. This is significant because as disk-based devices start to incorporate multiple processes like cell lysis, washing, and purification on a single disk, the chance of cross-contamination increases. In addition, in prior designs there is the possibility of fluids leaking out of vent holes located within the disk structure.

For example, in U.S. Pat. No. 6,319,469, each reaction chamber is vented to an air displacement channel located over each reaction chamber. If this venting strategy is used in a configuration where a first chamber is connected to an output chamber located radially outward of the first chamber, fluid transfer occurs from the first chamber to the output chamber. However, assuming a slower flow rate out of the output chamber (e.g., because of the presence of downstream valve, filter, channel restriction and/or microbeads), fluid accumulates in the output chamber and if the output chamber vent is located below the level of the liquid in the first chamber, liquid will leak out of this vent. In another possible configuration, where two chambers are independently connected to an output chamber, if the vent of the output chamber is located above the level of the two input chambers, there is a possibility of backflow into the upstream-located input chambers.

There thus is a need for a device and method that is capable of regulating fluid flow between the various features and elements contained in disk-based microfluidic devices. Such a device should permit the regulation of flow between various chambers or elements without the use of cumbersome and expensive mechanical or electrical valves. In particular, there is a need for a disk design that incorporates the ability to prevent cross-contamination between different chambers that have one or more common channels or outlets.

SUMMARY OF THE INVENTION

According to one embodiment of the invention, a microfluidic device includes a substrate configured for rotation about an axis, the substrate having a first chamber disposed therein. The microfluidic device includes an output chamber disposed in the substrate and located radially outward of the first chamber. A vent hole is provided that is operatively connected to the output chamber. The first chamber includes a fluid transfer channel in communication with the output chamber and a ventilation channel in communication with output chamber, wherein the ventilation channel is coupled to a radially inward portion of the first chamber.

In another aspect, a microfluidic device includes a substrate configured for rotation about an axis, the substrate having a first start chamber disposed therein. The microfluidic device includes an output chamber disposed in the substrate and located radially outward of the start chamber. A fluid transfer channel connects the first start chamber to the output chamber. A ventilation channel connects the output chamber to the first start chamber, the ventilation channel connecting at one end to a radially inward portion of the first start chamber and at an opposing end to a junction point on the output chamber. The device includes a vent hole operatively connected to the output chamber. The junction between the ventilation channel and the output chamber is located radially outward with respect to the level of fluid in the start chamber.

In another aspect of the invention, a method of regulating fluid flow in a microfluidic device includes providing a substrate configured for rotation about an axis, the substrate having first and second chambers disposed therein containing a liquid, the substrate further including an output chamber disposed in the substrate and located radially outward of the first and second chambers, the output chamber being operatively coupled to the first chamber via a fluid transfer channel and a ventilation channel, the output channel further being operatively coupled to the second chamber via a fluid transfer channel and a ventilation channel, the substrate also including a vent hole operatively connected to the output chamber, the substrate also including a output channel coupled to the output chamber. Rotation of the substrate at a first, low rotational speed transfers liquid from the first chamber to the output chamber but rotation of the substrate at the first, low rotational speed does not transfer fluid from the second chamber to the output chamber. Rotation of the substrate at a second, high rotational speed transfers liquid from the second chamber to the output chamber. According to the method, the substrate is then rotated at the first, low rotational speed to transfer liquid from the output chamber to the output channel. This last reduction in rotational speed primes the siphoning channel allowing fluid to exit the output chamber. The substrate may then be rotated at a higher rotational speed to empty the second chamber.

DETAILED DESCRIPTION OF THE ILLUSTRATED EMBODIMENTS

Figure 1:
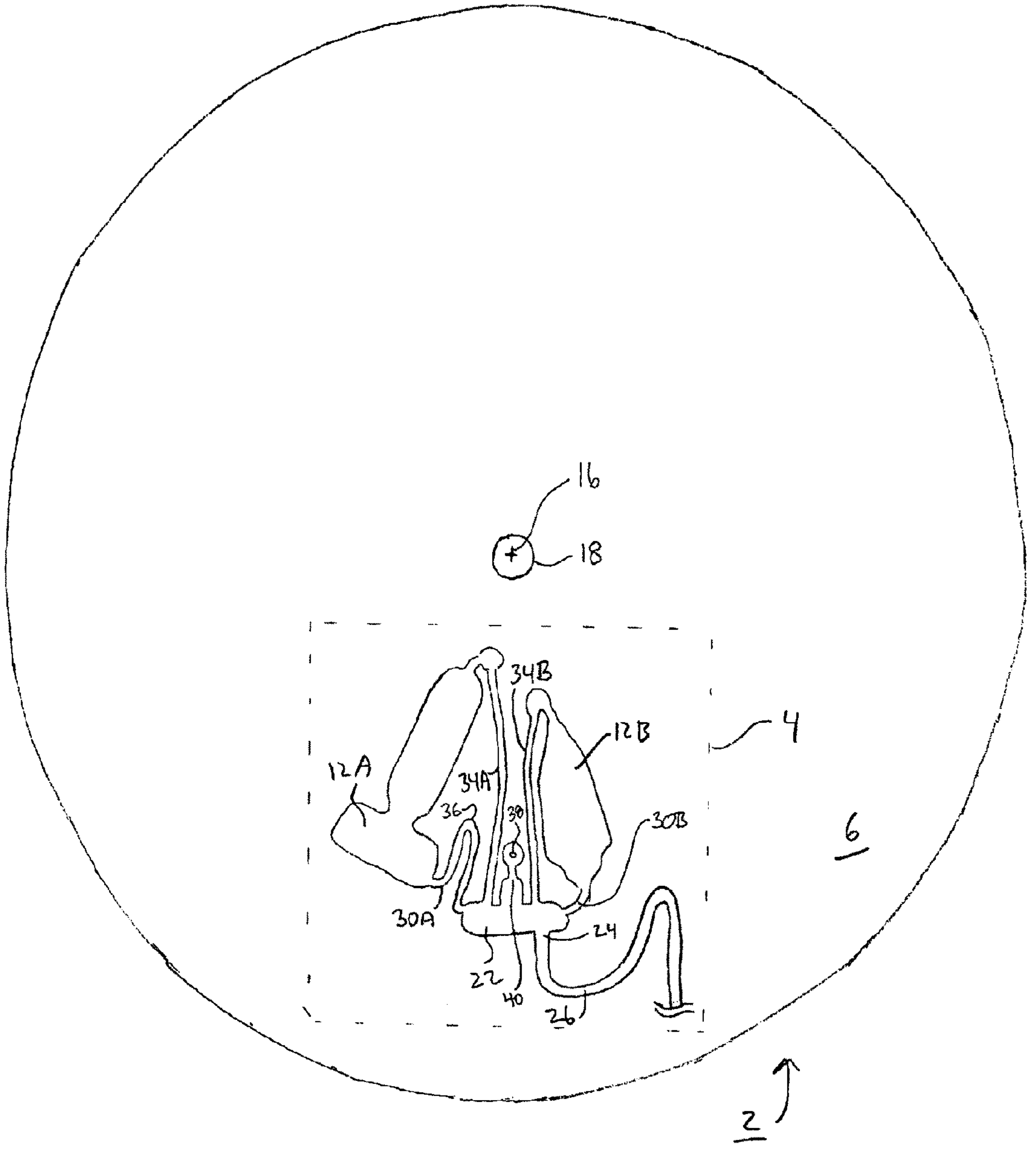
FIG. 1 illustrates a schematic representation of a centrifugal microfluidic system formed on a rotationally driven substrate according to one embodiment.

FIG. 1 illustrates a centrifugal microfluidic device 2 according to one embodiment. The microfluidic device 2 may include a number of microfluidic features 4 disposed in a substrate 6. Microfluidic feature 4 includes such structures as chambers, channels, vents, inlets, outlets, and other structures commonly found in microfluidic devices. The microfluidic feature 4 illustrated in FIG. 1 may, in reality, be smaller or larger than depicted in FIG. 1. Generally, the size of the feature 4 is not critical and there is no limitation on the size of the substrate 6. Further, the microfluidic devices 2 contemplated herein may include several or multiple different (or the same) microfluidic features 4 populated around the periphery of substrate 6.

As seen in FIG. 1, the microfluidic feature 4 includes multiple start chambers 12A, 12B (e.g., reservoirs) located within the substrate 6. In one aspect, the substrate 6 may include a polymer-based material that is formed into a circular or disk shape such as, for example, in the form of a compact disk (CD). As explained in detail below, the substrate 6 may be made of multiple layers of a polycarbonate material arranged in a sandwich-type arrangement to create the various microfluidic features. The substrate 6 is configured to be rotatable about an axis of rotation 16. As seen in FIG. 1, the axis of rotation 16 may coincide with an aperture 18 or hole located through the substrate 6 that is dimensioned to receive a rotatable spindle or drive shaft (not shown). As explained below, during operation of the microfluidic device 4, the substrate 6 is rotated is cyclical fashion about the axis of rotation 16. This may be accomplished from a rotating spindle or drive shaft that interfaces with the substrate 6 via the aperture 18. For example, drive systems found in commercially available DVD or CD players may be employed to provide the rotation motion to the substrate 6. Such devices are known to those skilled in the art and are not explained herein.

Still referring to FIG. 1, the microfluidic feature 4 includes an output chamber 22 or reservoir that is located radially outward with respect to the two start chambers 12A, 12B. As used herein, radially outward is a relative term meant to indicate that the particular location is located further away from the axis of rotation 16 of the substrate 6. Similarly, radially inward is meant to indicate that the particular location is located closer to the axis of rotation 16 of the substrate 6. The output chamber 22 may include an outlet 24 that is coupled to an output channel 26. As explained below, during certain conditions, fluid contained in the output chamber 22 is permitted to leave the output chamber 22 via the outlet 24 and into the output channel 26. The output channel 26 (or outlet 24) may be further coupled to other microfluidic features 4 for further operations. For example, in one aspect of the invention, a first start chamber 12A is configured to hold a fluid (not shown) that is a lysing agent. The second start chamber 12B is configured to hold a fluid (not shown) that is a washing agent. Many other configurations are contemplated. For example, one chamber 12A, 12B may hold a lysing agent while another chamber 12A, 12B may hold a washing or purification agent. Reagents or samples from a patient (e.g., bodily fluid such as plasma or some constituent of a bodily fluid) may also be contained in the chambers 12A, 12B. Generally, any liquid which is able to flow through the various microfluidic features 4 may be used.

Still referring to FIG. 1, each chamber 12A, 12B includes a respective fluid transfer channel 30A, 30B that connects respective first and second reservoirs 12A, 12B to the output chamber 22. As shown in FIG. 1, the fluid transfer channels 30A, 30B connect to the output chamber 22 at opposing side locations on the output chamber 22. FIG. 1 also illustrates respective ventilation channels 34A, 34B that connect the first and second reservoirs 12A, 12B to the output chamber 22. As seen in FIG. 1, the ventilation channels 34A, 34B connect to each chamber 12A, 12B at a top or a radially inward location. Opposing ends of the ventilation channels 34A, 34B connect to the top or radially inward portion of the output chamber 22 as seen in FIG. 1 (as opposed to radially outward portion of output chamber 22). The ventilation channel 34A that couples the first chamber 12A to the output chamber 22 includes a radially inward bend portion 36. The bend portion 36 is needed for the siphon valve aspect of the invention which prevents fluid from leaving the output chamber 22. Still referring to FIG. 1, the device 2 includes a vent hole 38 or the like that is in fluidic communication via channel 40 or the like with respect to the output chamber 22. The vent hole 38 is located radially inward with respect to the junction between the ventilation channels 34A, 34B and the output chamber 22. The vent hole 38 is bidirectional in that air can pass into or out of vent depending on the rotational state of the substrate 6. For example, air can leave the vent hole 38 when the device 2 is the state illustrated in FIG. 3C whereby some fluid enters channel 40. Conversely, air can enter the vent hole 38 in the state illustrated in FIG. 3D when the substrate 6 is rotated at a slow rotational speed. Air enters channel 40 and output chamber 22.

Figure 2:
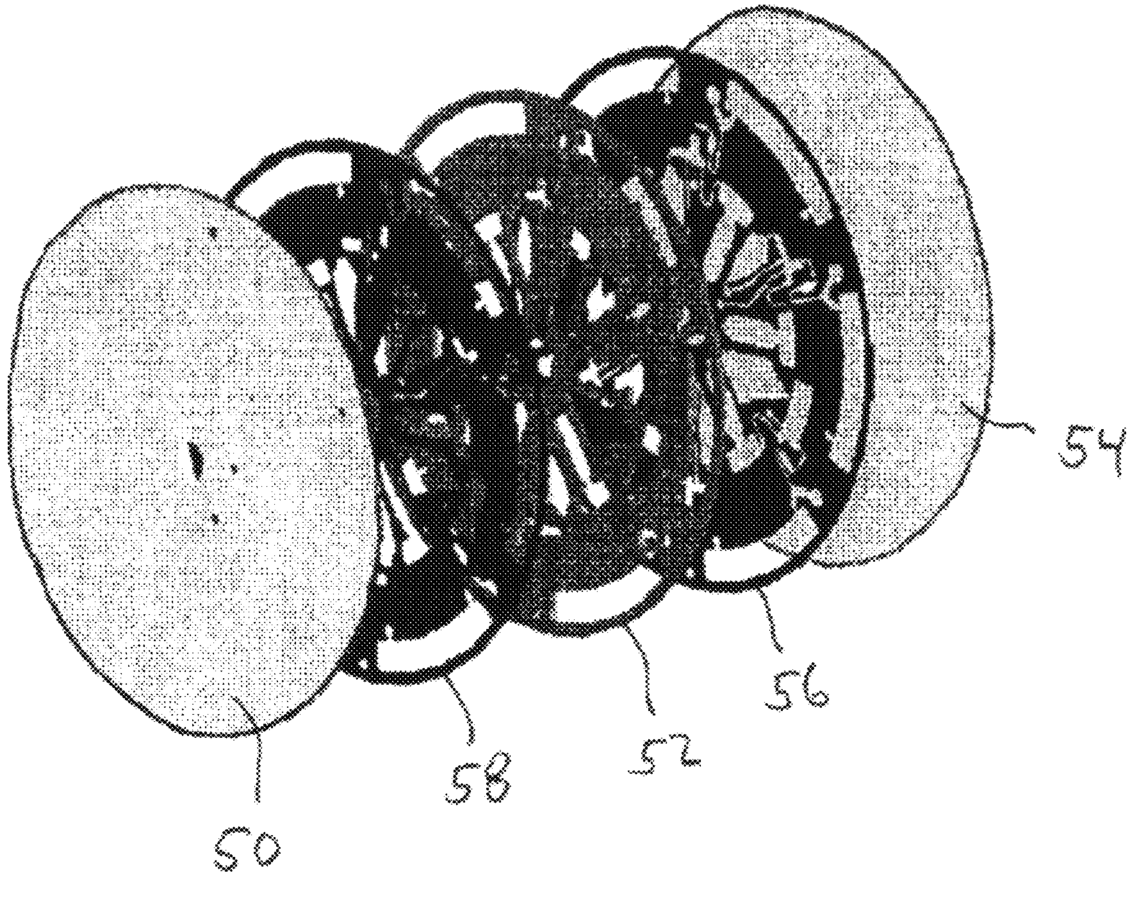
FIG. 2 illustrates one exemplary embodiment of a substrate formed as a multi-layer structure.

FIG. 2 illustrates one exemplary construction of the microfluidic device 2. As seen in FIG. 2, the substrate 6 is made of three (3) polycarbonate disks 50, 52, 54 and two (2) intermediate pressure sensitive adhesive layers 56, 58. The layout of the various microfluidic features 4 may be designed using conventional design software such as, for instance, SOLIDWORKS or AUTOCAD. A computer numerically controlled (CNC) milling machine mills the various features and cuts the polycarbonate disks 50, 52, 54. Alignment holes may be drilled in one or more the disks 50, 52, 54 at the same location so that each disk 50, 52, 54 may be properly oriented in the radial direction when the composite structure is formed. One of the disks 50 acts as a cover disk. For instance, the cover disk 50 may be made from 0.6 mm thick polycarbonate. The middle disk 52 may also be made from polycarbonate although the thickness is typically greater than the cover disk 50. For instance, the middle disk 52 may have a thickness of around 3.175 mm. The middle disk 52 contains the various chambers 12A, 12B, 22. The bottom disk 54 may also be formed from polycarbonate and has a thickness like that of cover disk 50 (e.g., 0.6 mm).

The pressure sensitive adhesive layers 56, 58 may include 100 μm thick sheets of double-sided adhesive film. For example, the pressure sensitive adhesive layers 56, 58 may be obtained from FLEXcon Corporation, located at 1 FLEXcon Industrial Park, Spencer, Mass. 01562-2642. Exemplary pressure sensitive adhesive layers 56, 58 include FLEX mount DFM 200 clear V-95 available from FLEXcon. The various designs/features in the pressure sensitive adhesive layers 56, 58 may be created using software-based design tools. The instructions may then loaded into a roll-feed cutter plotter (e.g., using SignGo software available from Wissen UK Inc. Ltd., United Kingdom). For example, a Western Graphtec CR2000-60 (Santa Ana, Calif.) roll-feed cutter plotter may be used to cut features in the pressure sensitive adhesive layers 56, 58. Channel features are cut in one pass though the top release film and the middle adhesive layer, but not through the bottom supporting release film.

The top disk 50 includes any vent holes including vent hole 38. The middle disk 52, which is thicker, contains the chambers such as chambers 12A, 12B, and output chamber 22. The channels such as the fluid transfer channels 30A, 30B, the ventilation channels 34A, 34B, and the output channel 26 are formed in the upper adhesive layer 50. The width of the various channels, e.g., channels 26, 34A, 34B, 34A, and 34B are typically less than 1 mm. To form the final composite structure, the pressure sensitive adhesive layers 56, 58 are placed between the disks 50, 52, 54 in alignment (using alignment holes) and the entire stack is then bonded together. It should be understood that the dimensions given above are illustrative only and other dimensions may work in accordance with the inventive concepts described herein.

By incorporating the ventilation channels 34A, 34B along with the common vent hole 38 in the microfluidic device 2, when the substrate 6 is rotationally driven about the axis of rotation 16, regulated flow between the start chambers 12A, 12B and the output chamber 22 can occur. In particular, fluid may be able to flow into the output chamber 22, where mixing may occur between the fluids initially contained in the respective start chambers 12A, 12B without fear of cross contamination of the "virgin" start chambers 12A, 12B. For example, if the ventilation channels 34A, 34B and the common vent hole 38 were removed from the device 2, the fluid contained in the output chamber 22 (which may include a mixture of fluid from chambers 12A, 12*b*) could flow in reverse or retrograde fashion to contaminate the liquid contained in start chambers 12A, 12B. For instance, assume that ventilation channels 34A, 34B and the common vent hole 38 were omitted from the device 2, and that start chamber 12A was filled with lysate or lysis material and start chamber 12B was filled with a wash or an elution material with each chamber 12A, 12B having respective vent holes (not shown). In this situation, wash material from chamber 12B may enter the output chamber 22 and flow back to the other start chamber 12A, thereby contaminating start chamber 12A with wash. Similarly, lysate or lysis material from chamber 12A may enter the output chamber 22 and flow back to the other start chamber 12B, thereby contaminating start chamber 12B with lysate or lysis material. The present invention avoids this cross-contamination problem through the use of fluid regulation via ventilation channels 34A, 34B, and common vent hole 38.

For a design without flow regulation, fluid transfer will occur from start chamber 12B to output chamber 22, thence to chamber 44 and output channel 26. However, assuming a slower flow rate through chamber 44 (for instance, if chamber 44 were full of microbeads), fluid accumulates in chamber 44 and backs up into output chamber 22. Given the reference frame of radially inward as "higher" and radially outward as "lower," the fluid will continue to rise higher until it reaches the same level as the starting fluid in start chamber 12B, as that fluid will have higher "potential energy" if it is higher and continue to drain out of start chamber 12B. Given the large volume of start chamber 12B compared with chamber 44 and output chamber 22, it is easy to see that output chamber 22 will completely overflow, leaking fluid out of venting hole 38. If vent hole 38 were moved "higher," the fluid would backflow in retrograde fashion through siphon valve 36 back into start chamber 12A, causing cross-contamination. It should also be noted that fluid cannot be trapped in chamber 44 by siphon valve 26, since there is no guarantee that the fluid level will remain below the bend portion in output channel 26. Therefore, the regulation of the fluid level in output chamber 22 at the level of the junction of ventilation channel 34B and output chamber 22 is useful not only in preventing cross-contamination into start chamber 12A, but also to ensure that the siphon valve in output channel 26 is not surpassed.

The microfluidic design described herein uses the ventilation channels 34A, 34B to equilibrate the respective levels of fluid in the respective start chamber 12A, 12B depending on the rotational speed of the substrate 6. For instance, with respect to the first start chamber 12A and the first ventilation channel 34A, upon rotation of the substrate 6 at sufficient volume to fill the output chamber 22, an equilibrium level will be reached when the negative pneumatic pressure in the start chamber 12A equals the pressure of the fluid that is above the fluid level in the output chamber 22 (i.e., fluid level in the first ventilation channel 34A is the same height as fluid level in the first chamber 12A as seen in FIG. 3C). When this equilibrium level is reached, fluid flow from the start reservoir 12A to the output chamber 22 ceases. Fluid flow from the start chamber 12A to the output chamber 22 only resumes once the fluid level in output chamber 22 is below the junction of the output chamber 22 and the first ventilation channel 34A. In this regard, the flow rates of output chamber 22 and the start chamber 12A is modulated by the first ventilation channel 34A and the common vent hole 38. In a similar fashion, the flow rate of the output chamber 22 and the start chamber 12B is modulated by the second ventilation channel 34B. The junction between the ventilation channel 34A and the output chamber 22 is designed to be radially-outward with respect to the level of fluid contained in the start chamber 12A. Because fluid flows from the radially-inward to the radially-outward direction, regulation of the fluid level at a radially-outward location prevents fluid transfer in the reverse direction.

The microfluidic device 2 is thus a self-regulating microfluidic system in which a number of microfluidic elements or features (e.g., reservoirs, chambers, channels and the like) may be employed on a single substrate 6 and connected to each other by ventilation channels 34A, 34B and fluid transfer channels 30A, 30B. The self-regulating system is thus able to avoid the problems of cross-contamination. The system accomplishes this regulation by negative feedback whereby excess fluid (which passes into the ventilation channels 34A, 34B) will stop fluid transfer from the starting chambers 12A, 12B to the output chamber 22. The system and device 2 described herein has applications for integrated centrifugal microfluidic sample preparation, cellular and chemical analysis, clinical, and medical diagnosis applications.

Figure 3A:
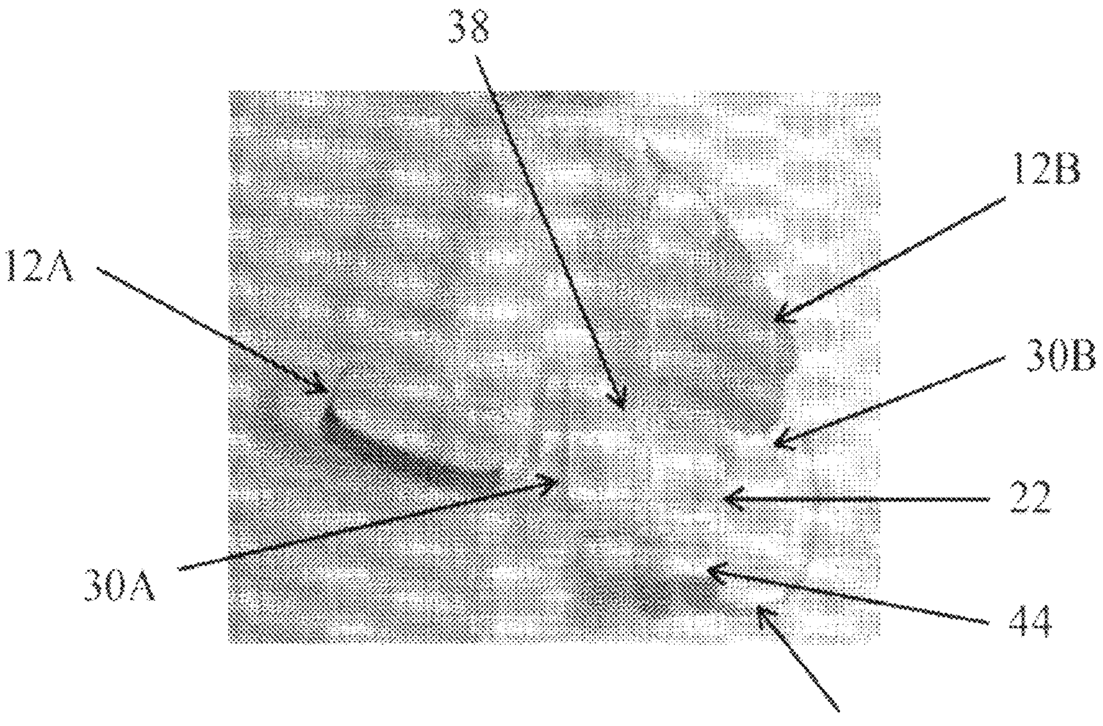
FIG. 3A is a photographic image of a system like that disclosed in FIG. 1 that is spun at 100 rpm.
Figure 3B:
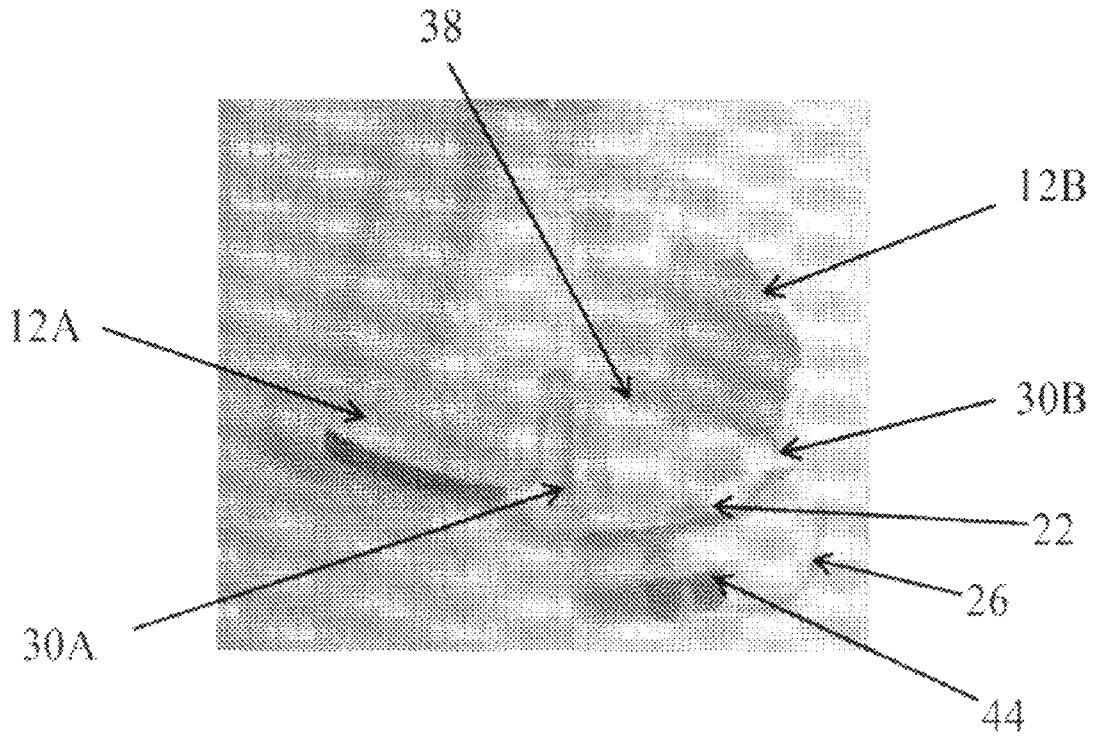
FIG. 3B is a photographic image of a system like that disclosed in FIG. 1 that is spun at 1500 rpm.
Figure 3C:
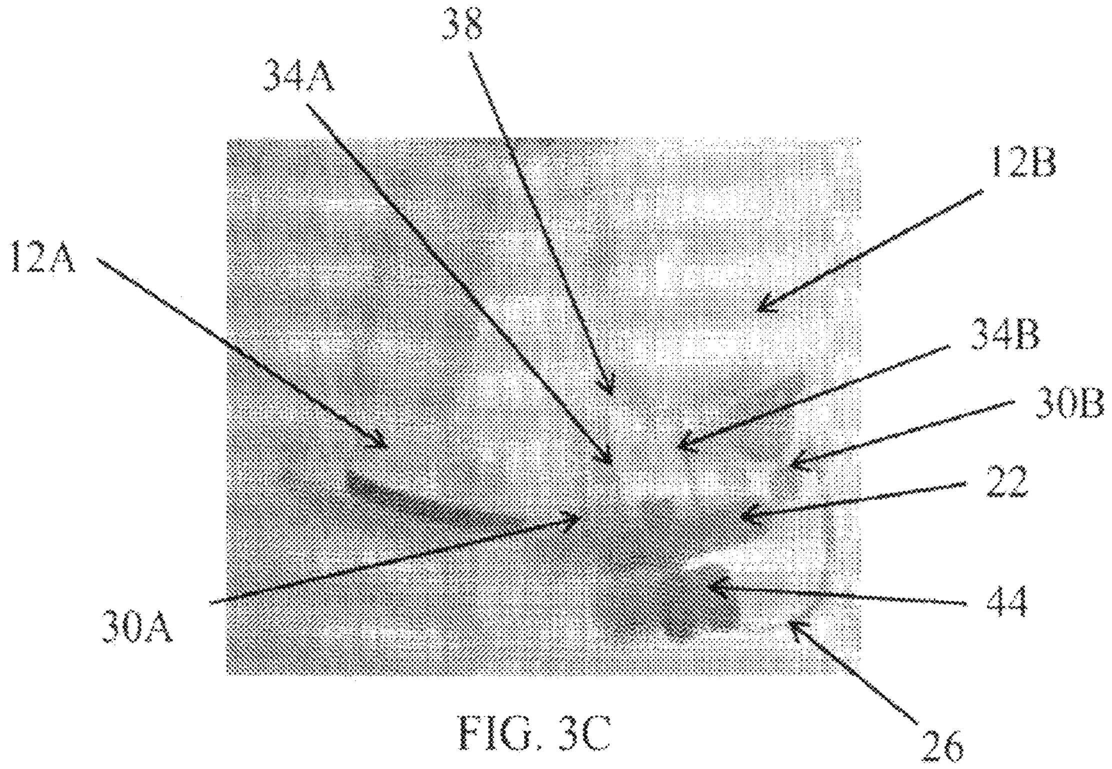
FIG. 3C is a photographic image of a system like that disclosed in FIG. 1 that is spun at 1500 rpm.

FIGS. 3A-3G illustrate photographic images taken of a microfluidic feature 4 like that disclosed in FIG. 1. The photographic images are taken at various angular velocities. Different colored fluids (water with food coloring) were loaded into the two starting chambers 12A, 12B with starting chamber 12A containing a darker fluid. The device 2 was rotated at an initial angular velocity of 100 rpm. As seen in FIG. 3A, in this initial condition there is fluid in the start chamber 12B and none of its respective fluid in the output chamber 22. The fluid transfer channel 30B coupling the start chamber 12B and the output chamber 22 acts as a capillary valve that prevents fluid transfer at low rotational speeds. At the low rotational speed, however, fluid from the staring chamber 12A enters the fluid transfer channel 30A. With reference to FIGS. 3C-3G, the height or radial location of the junction between ventilation channel 34B and output chamber 22 determines the fluid level in the output chamber 22 at which regulation occurs. In one aspect, this junction may be located radially outward with respect to the start chamber 12B. Generally, the microfluidic feature 4 may be designed such that the fluid level in the output chamber 22 can be regulated at an arbitrary level with respect to the junction between fluid transfer channel 30B and the output chamber 22.

FIGS. 3A-3G illustrate an optional chamber 44 that is located downstream of the output chamber 22 and upstream of the output channel 26. In particular, fluid flows from the output chamber 22 to the chamber 44 and then to output channel 26. The optional chamber may be used for solid phase nucleic acid extraction in which glass or silica beads are located in the chamber 44. Solid phase extraction may be used to concentrate nucleic acid (e.g., DNA) from a sample for subsequent elution and processing. Typically, this involves: (1) adsorbing DNA to silica beads in the presence of chaotropic salts, (2) washing away contaminants with an alcohol solution, and (3) eluting DNA in a low-salt solution. Of course, it should be understood that chamber 44 is entirely optional.

FIG. 3B illustrates the device 2 at a high rotational speed, namely, a rotational speed of 1500 rpm. As can be seen from FIG. 3B, fluid is transferred from the start chamber 12B to the output chamber 22. Generally, any rotational speed capable of bursting the capillary valve located in the fluid transfer channel 30B will suffice. Liquid will not pass a capillary valve so long as pressure at the meniscus is less than or equal to the capillary barrier pressure. A "burst frequency" is reached when the rotational frequency of the substrate 6 is such that the pressure at the meniscus exceeds the capillary barrier pressure. The burst frequency may be modified and altered depending on the particular construction and geometry of the fluid transfer channel 30B. In some cases, this may be in excess of about 1000 rpm. In the state shown in FIG. 3B, the fluid level in the output chamber 22 has not yet reached the level of the ventilation channel 34B. Fluid that enters the output chamber 22 passes to chamber 44. Outward flow from chamber 44 is blocked due to the siphon valve located at the output channel 26. Once the chamber 44 is filled up (as seen in FIG. 3C), output chamber 22 fills up. In the illustrated device 2, there are two separate siphon valves. A first siphon valve located in the bend portion 36 of the fluid transfer channel 30A restricts flow from the first start chamber 12A. A second siphon valve in the output channel 26 restricts flow from the output chamber 22.

FIG. 3C illustrates continued rotation of the device 2 at a rotational speed of 1500 rpm. In this image, the fluid level in the output chamber 22 surpasses the junction between the ventilation channel 34B and the output chamber 22 and, consequently, liquid is drawn up the ventilation channel 34B. This rise in the liquid level within the ventilation channel 34B continues until an equilibrium level is reached between the pressure in the start chamber 12B and the pressure of the fluid column in the ventilation channel 34B. As seen in FIG. 3C, this occurs when the upper level of level of the liquid in the ventilation channel 34B is approximately equal to the level of liquid contained in the chamber 12B. Again, because of the high rotational speed, there is no outflow from the output chamber 22 because, in this particular embodiment, the presence of the siphon valve located at the output channel 26 regulates fluid flow from chamber 44. For example, this steady-state condition illustrated in FIG. 3C may be used to incubate chamber 44 with wash or elutant from start chamber 12B.

It should be emphasized that the fluid that is in the output chamber 22 (which may contain a mixture of fluid from start chambers 12A, 12B) is prevented from returning or contaminating start chamber 12B. Fluid transfer from the start chamber 12A to the output chamber 22 is prevented because the fluid level in the output chamber 22 is regulated at a level below that of the fluid contained in the start chamber 12A. Further, as seen in FIG. 3C, the fluid that is contained in the output chamber 22 while able to partially flow upward in the ventilation channel 34A, is unable to reach the start chamber 12A. The fluid contained in the output chamber 22 is thus prevented from entering start chamber 12A. Cross-contamination is prevented because fluid flow occurs in the radially-inward to radially-outward direction and the presence of the common vent hole 38 and the respective ventilation channels 34A, 34B are able to modulate flow from the respective start chambers 12A, 12B to the output chamber 22.

Figure 3D:
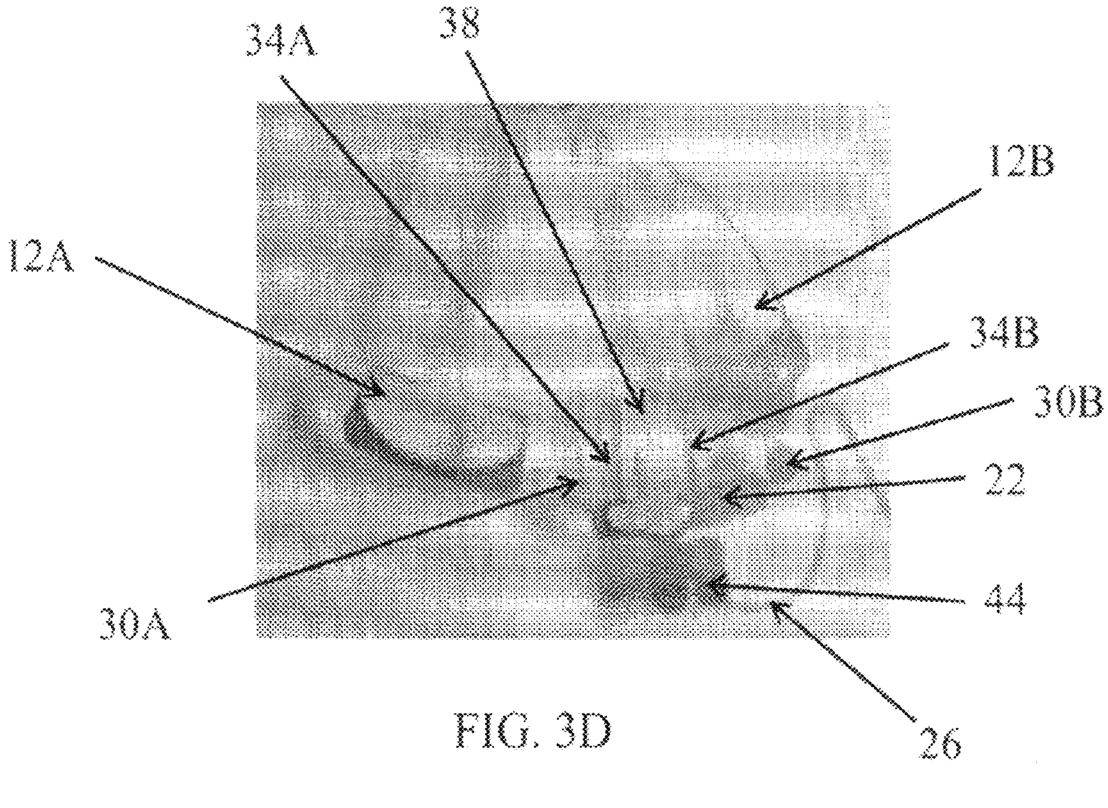
FIG. 3D is a photographic image of a system like that disclosed in FIG. 1 that is spun at 100 rpm.

Turning now to FIG. 3D, a photographic image is taken of the microfluidic device 2 being rotated at low rotational speed of 100 rpm. At the lower rotational speed, the fluid contained in the microfluidic features 4 is now subject to a significantly reduced centrifugal force. While 100 rpm is illustrated, other low rotational speeds are contemplated such as those below about 200 rpm. The fluid level in the output chamber 22 is reduced because the pressure induced by centrifugal force has decreased, drawing air through the vent hole 38 (as seen by bubble in output chamber 22 in FIG. 3D). Further, the level of fluid within both ventilation channels 34A, 34B rises, leading the upper level of fluid in the chambers 12A, 12B to form a concave, meniscus-like surface in order to try to equalize the level of fluid with that in the ventilation channels 34A, 34B. Because of the reduction in the rotational speed of the substrate 6 from a high rotational speed to a low rotational speed, the siphon located in output channel 26 which regulates outflow from chamber 44 has been "primed." Consequently, fluid outflow from the output chamber 22 via chamber 44 and output channel 26 is now permitted as seen by the passage of fluid down the output channel 26 in FIG. 3D.

Figure 3E:
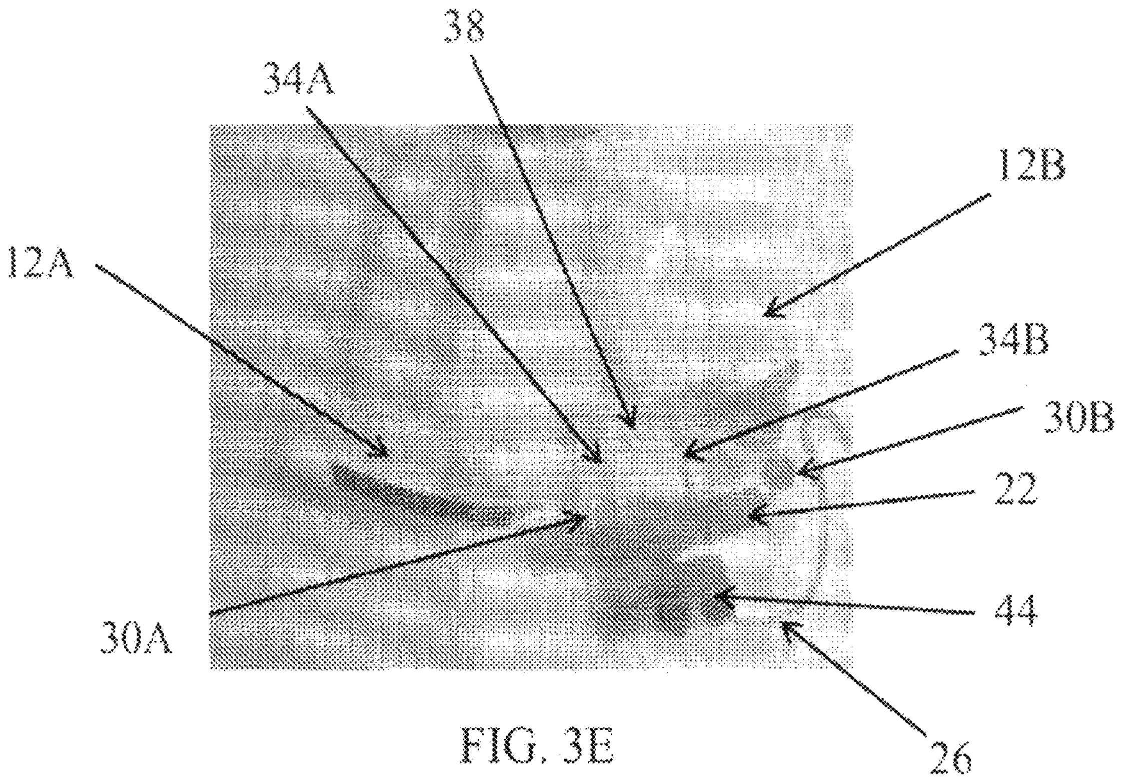
FIG. 3E is a photographic image of a system like that disclosed in FIG. 1 that is spun at 1500 rpm.

Turning now to FIG. 3E, a photographic image of the microfluidic device 2 is illustrated after the rotational speed has been increased from the low 100 rpm rate to the higher 1500 rpm rate. Because the siphon has been primed, the flow of fluid from the chamber 12B to the output chamber 22 and subsequently to the output channel 26 continues. The rate of fluid outflow from the output chamber 22 is matched by the transfer of fluid from the chamber 12B to the output chamber 22. FIG. 3E illustrates the dynamic interaction between the outflow of output chamber 22 and fluid transfer between start chamber 12B and output chamber 22. When the fluid level in the output chamber 22 drops below the junction between the ventilation channel 34B and the output chamber 22 as a result of outflow through output channel 26, the fluid in the ventilation channel 34B drains out and air is permitted to enter the start chamber 12B. Fluid flow between start chamber 12B and output chamber 22 immediately resumes until the fluid level in the output chamber 22 again reaches the junction between the ventilation channel 34B and the output chamber 22 and fluid is taken up ventilation channel 34B. The dynamic interaction the junction between the ventilation channel 34B and the output chamber 22 is illustrated by the presence of bubbles in ventilation channel 34B as the result of the competing desires to uptake air and liquid. Further, as seen in FIG. 3E, the fluid level is precisely located at the junction between the ventilation channel 34B and the output chamber 22, as compared to FIG. 3C in which the fluid level is shown as about halfway up 34B.

Figure 3F:
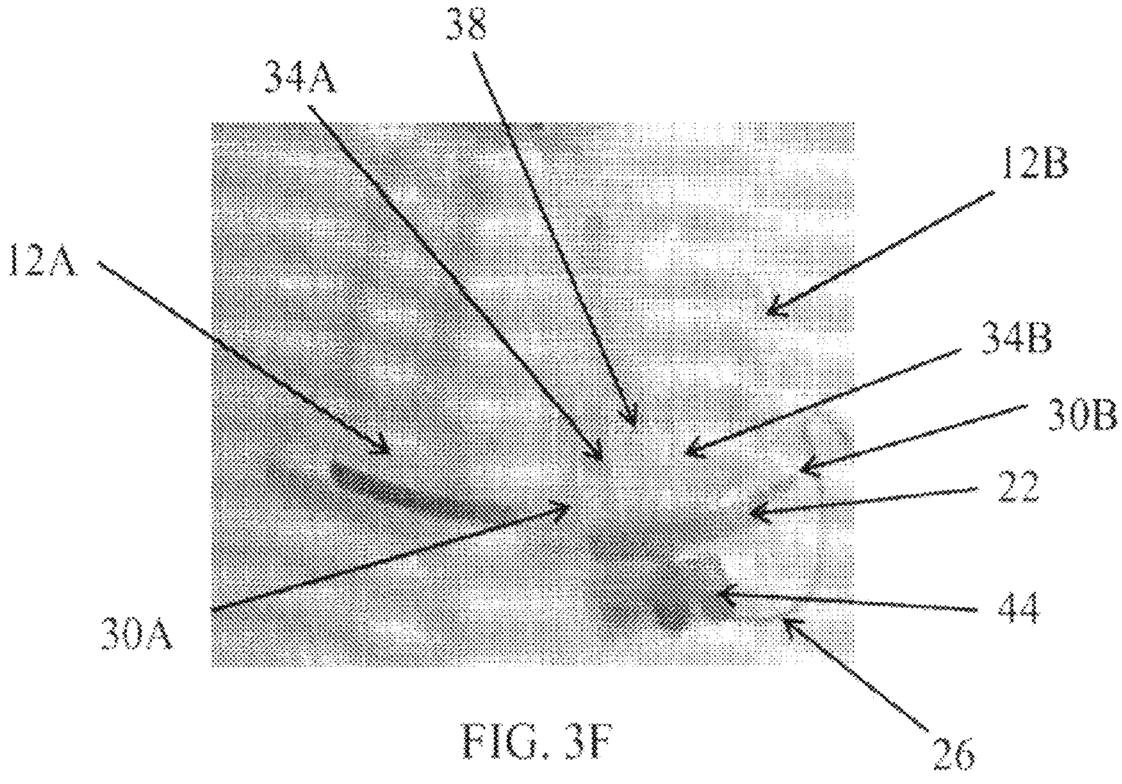
FIG. 3F is a photographic image of a system like that disclosed in FIG. 1 that is spun at 1500 rpm.
Figure 3G:
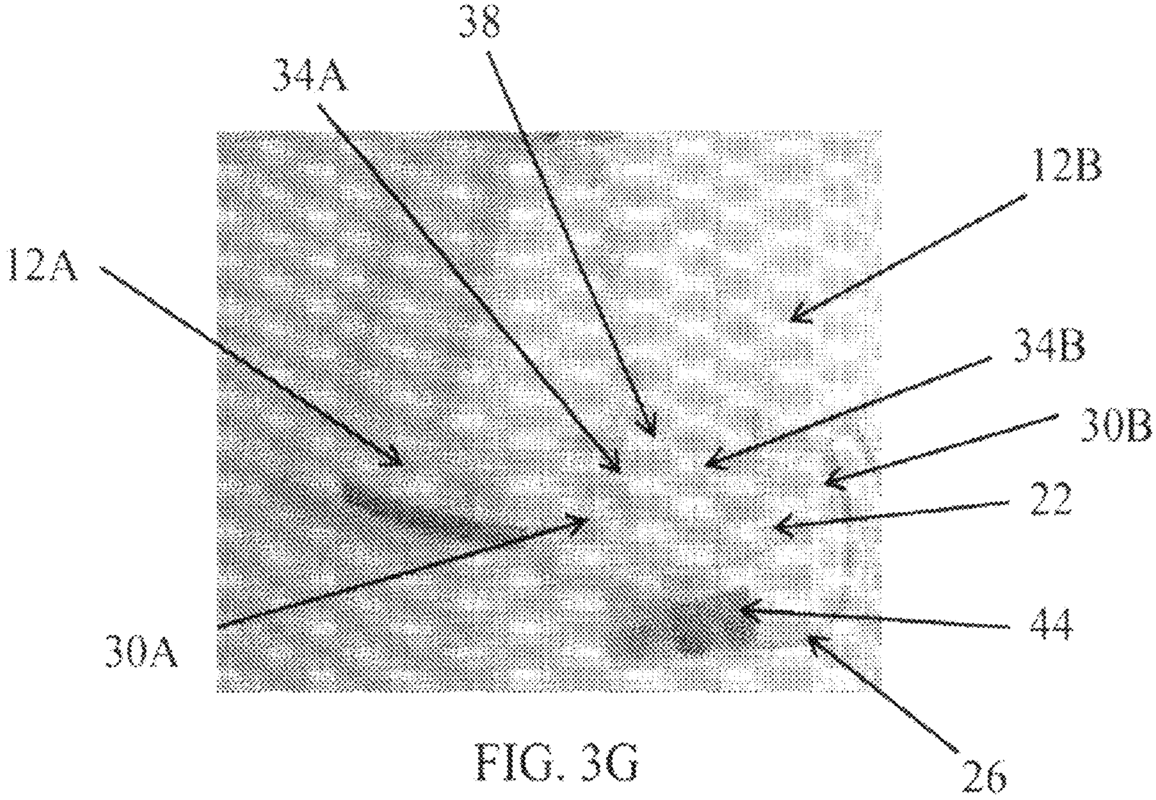
FIG. 3G is a photographic image of a system like that disclosed in FIG. 1 that is spun at 1500 rpm.

FIG. 3F illustrates a photographic image of the microfluidic device 2 rotated at 1500 rpm. FIG. 3F illustrates a state when start chamber 12B has been completely drained, thereby permitting the fluid level in the output chamber 22 to fall below the junction of the ventilation channel 34B and the output chamber 22. Because there is no longer any inflow to the output chamber 22, the dynamic interaction between start chamber 12B and the output chamber 22 is no longer maintained. FIG. 3G illustrates transfer of fluid from the output chamber 22 to the chamber 44, which empties via output channel 26.

While embodiments of the present invention have been shown and described, various modifications may be made without departing from the scope of the present invention. The invention, therefore, should not be limited, except to the following claims, and their equivalents. Further, U.S. Provisional Patent Application No. 60/916,774 filed on May 8, 2007, to which this Application claims priority, is incorporated by reference as if set forth fully herein.

What is claimed is:

1. A microfluidic device comprising:

a substrate configured for rotation about an axis, the substrate having a first chamber and a second chamber disposed therein, the first and second chambers configured to carry a liquid;

an output chamber disposed in the substrate and located radially outward of the first chamber and the second chamber;

a vent hole operatively connected to the output chamber;

wherein the first chamber includes a fluid transfer channel in communication with the output chamber and a ventilation channel, absent a capillary junction, in communication with the output chamber, the ventilation channel being coupled to a radially inward portion of the first chamber and configured to contain liquid from the output chamber and wherein the second chamber includes a fluid transfer channel in communication with the output chamber and a ventilation channel in communication with the output chamber, the ventilation channel being coupled to a radially inward portion of the second chamber and configured to contain liquid from the output chamber.

2. The microfluidic device of claim 1, further comprising an outlet channel in communication with the output chamber.

3. The microfluidic device of claim 1, wherein the fluid transfer channel of the first chamber includes at least one radially inward bend.

4. The microfluidic device of claim 1, wherein the ventilation channel of the first chamber connects to the output chamber at a location that is radially outward with respect to the location of the vent hole.

5. The microfluidic device of claim 1, wherein the first chamber holds one of a lysing or washing agent.

6. The microfluidic device of claim 1, wherein one of the first and second chambers holds one of a lysing or washing agent and the other of the first and second chambers holds the other of a lysing or washing agent.

7. The microfluidic device of claim 1, wherein the fluid transfer channel of the second chamber comprises a capillary valve.

8. The microfluidic device of claim 1, further comprising a drive device configured to rotate the substrate about the axis.

9. A microfluidic device comprising:

a substrate configured for rotation about an axis, the substrate having a first start chamber disposed therein, the first start chamber configured to hold a first liquid, the substrate further having a second start chamber disposed therein and configured to hold a second liquid;

an output chamber disposed in the substrate and located radially outward of the first start chamber and the second start chamber;

a first fluid transfer channel connecting the first start chamber to the output chamber;

a second fluid transfer channel connecting the second start chamber to the output chamber;

a first ventilation channel absent a capillary junction, connecting the output chamber to the first start chamber, the first ventilation channel connecting at one end to a radially inward portion of the first start chamber and at an opposing end to a junction point on the output chamber, the first ventilation channel configured to carry liquid from the output chamber partially therein;

a second ventilation channel, absent a capillary junction, connecting the output chamber to the second start chamber, the second ventilation channel connecting at one end to a radially inward portion of the second start chamber and at an opposing end to a junction point on the output chamber, the second ventilation channel configured to carry liquid from the output chamber partially therein;

a vent hole operatively connected to the output chamber; and wherein the junction between the first ventilation channel and the output chamber is located radially outward with respect to the level of first fluid in the first start chamber and wherein the junction between the second ventilation channel and the output chamber is located radially outward with respect to the level of second fluid in the second start chamber.

10. The microfluidic device of claim 9, further comprising one or more chambers coupled to the output chamber via respective fluid transfer channels.

11. The microfluidic device of claim 9, further comprising a chamber coupled to an output of the output chamber.

12. The microfluidic device of claim 11, wherein the chamber coupled to the output of the output chamber contains a plurality of beads configured for solid phase nucleic acid extraction.

13. The microfluidic device of claim 12, further comprising an output channel coupled to the output chamber containing the plurality of beads configured for solid phase nucleic acid extraction.

14. The microfluidic device of claim 9, wherein the first start chamber holds a lysing agent and the second start chamber holds the washing agent.

15. The microfluidic device of claim 9, further comprising a drive device configured to rotate the substrate about the axis.

* * * * *